United States Patent
Jeon et al.

(10) Patent No.: US 11,946,051 B2
(45) Date of Patent: Apr. 2, 2024

(54) COMPOSITION FOR PREVENTING OR TREATING KELOIDS OR HYPERTROPHIC SCARS

(71) Applicant: Tego Science Inc., Seoul (KR)

(72) Inventors: Saewha Jeon, Seoul (KR); Ho Yun Chung, Daegu (KR); Na Ra Oh, Seoul (KR); Yun Hee Kim, Seoul (KR); Jikhyon Han, Seoul (KR); Hyun Ah Moon, Seoul (KR)

(73) Assignee: Tego Science Inc., Seoul (KR)

( * ) Notice: Subject to any disclaimer, the term of this patent is extended or adjusted under 35 U.S.C. 154(b) by 0 days.

(21) Appl. No.: 17/990,757

(22) Filed: Nov. 21, 2022

(65) Prior Publication Data

US 2023/0124032 A1    Apr. 20, 2023

Related U.S. Application Data

(62) Division of application No. 16/639,760, filed as application No. PCT/KR2019/017039 on Dec. 4, 2019, now abandoned.

(30) Foreign Application Priority Data

Sep. 24, 2019 (KR) .................. 10-2019-0117157

(51) Int. Cl.
*C07H 21/02* (2006.01)
*A61K 31/7105* (2006.01)
*A61K 31/713* (2006.01)
*C07H 21/04* (2006.01)
*C12N 15/113* (2010.01)
*G01N 33/68* (2006.01)

(52) U.S. Cl.
CPC ........ *C12N 15/113* (2013.01); *A61K 31/7105* (2013.01); *A61K 31/713* (2013.01); *G01N 33/6881* (2013.01); *G01N 33/6893* (2013.01); *C12N 2310/14* (2013.01); *G01N 2500/04* (2013.01); *G01N 2800/20* (2013.01)

(58) Field of Classification Search
CPC .......................... C12N 15/113; C12N 2310/14
See application file for complete search history.

(56) References Cited

U.S. PATENT DOCUMENTS

| | | |
|---|---|---|
| 7,691,997 B2 | 4/2010 | Khvorova et al. |
| 2009/0220488 A1 | 9/2009 | Gardner |
| 2015/0224132 A1 | 8/2015 | Appleman |
| 2021/0388352 A1 | 12/2021 | Jeon et al. |

FOREIGN PATENT DOCUMENTS

| | | |
|---|---|---|
| JP | 2016-532694 | 10/2016 |
| KR | 10-1505294 | 3/2015 |
| KR | 10-1697396 | 1/2017 |
| KR | 10-2017-0081962 | 7/2017 |
| WO | WO 2012/106508 | 8/2012 |
| WO | WO 2017/123046 | 7/2017 |
| WO | WO 2018/078624 | 5/2018 |

OTHER PUBLICATIONS

Final Official Action dated Aug. 22, 2022 From the US Patent and Trademark Office Re. U.S. Appl. No. 16/639,760. (9 Pages).
International Search Report and the Written Opinion dated Jul. 14, 2020 From the International Searching Authority Re. Application No. PCT/KR2019/017039 and Its Translation of Search Report Into English. (12 Pages).
Notice of Reasons for Rejection dated Jan. 11, 2022 From the Japan Patent Office Re. Application No. 2020-509485.
Official Action dated Mar. 18, 2022 from US Patent and Trademark Office Re. U.S. Appl. No. 16/639,760. (17 pages).
Restriction Official Action dated Nov. 22, 2021 from US Patent and Trademark Office Re. U.S. Appl. No. 16/639,760. (9 pages).
Bertrand et al. "Comparision of Antisense Oligonucleotides and siRNAs in Cell Culture and in Vivo", Biochemical and Biophysical Research Communications, 296(4): 1000-1004, Aug. 30, 2002.
Elbashir et al. "Functional Anatomy of siRNAs for Mediating Efficient RNA in Drosophila Melanogaster Embryo Lysate", The EMBO Journal, 20(23):6877-6888, Dec. 3, 2001.
Li et al. "MRP1 Knockdown Down-Regulates the Deposition of Collagen and Leads to A Reduced Hypertrophic Scar Fibrosis", Journal of Molecular Histology, 46(4-5): 357-364, Published Online Jun. 20, 2015.
Liang et al. "Systematical Analysis of Survival-Associated Alternative Splicing Signatures uncovers Prognostic Predictions for Head and Neck Cancer", Journal of Cellular Physiology, 234: 15836-15846, 2019.

*Primary Examiner* — Amy H Bowman

(57) ABSTRACT

The present invention relates to a pharmaceutical composition for preventing or treating hypertrophic scars. The present inventors have found that the inhibition of expression of TXNDC5, PRRC1, S100A11, Galectin 1, Filamin A, eIF-5A, Annexin A2, and FABP5 can be a new target for improving and treating hypertrophic scars. In the present invention, TXNDC5-, PRRC1-, S100A11-, Galectin 1-, Filamin A-, eIF-5A-, Annexin A2-, and FABP5-specific siRNAs were constructed to determine the probability of treating the hypertrophic scars. As a result, the knockdown of the protein or a gene encoding the protein induces apoptosis in the hypertrophic scars and reduces collagen expression, which can be very useful in treating wounds.

1 Claim, 2 Drawing Sheets
Specification includes a Sequence Listing.

SEQUENCE LISTING

```
Sequence total quantity: 8
SEQ ID NO: 1            moltype = RNA  length = 21
FEATURE                 Location/Qualifiers
misc_RNA                1..21
misc_feature            1..21
                        note = TXNDC5 siRNA sense
source                  1..21
                        mol_type = other RNA
                        organism = synthetic construct
SEQUENCE: 1
ggccctaact agagttctat t                                              21

SEQ ID NO: 2            moltype = RNA  length = 21
FEATURE                 Location/Qualifiers
misc_RNA                1..21
misc_feature            1..21
                        note = TXNDC5 siRNA antisense
source                  1..21
                        mol_type = other RNA
                        organism = synthetic construct
SEQUENCE: 2
tagaactcta gttagggcct t                                              21

SEQ ID NO: 3            moltype = RNA  length = 21
FEATURE                 Location/Qualifiers
misc_RNA                1..21
misc_feature            1..21
                        note = PRRC1(1) siRNA sense
source                  1..21
                        mol_type = other RNA
                        organism = synthetic construct
SEQUENCE: 3
caagaagacc ctagaattat t                                              21

SEQ ID NO: 4            moltype = RNA  length = 21
FEATURE                 Location/Qualifiers
misc_RNA                1..21
misc_feature            1..21
                        note = PRRC1(1) siRNA antisense
source                  1..21
                        mol_type = other RNA
                        organism = synthetic construct
SEQUENCE: 4
taattctagg gtcttcttgt t                                              21

SEQ ID NO: 5            moltype = RNA  length = 21
FEATURE                 Location/Qualifiers
misc_RNA                1..21
misc_feature            1..21
                        note = PRRC1(2) siRNA sense
source                  1..21
                        mol_type = other RNA
                        organism = synthetic construct
SEQUENCE: 5
tatcaaatct ggaggtgaat t                                              21

SEQ ID NO: 6            moltype = RNA  length = 21
FEATURE                 Location/Qualifiers
misc_RNA                1..21
misc_feature            1..21
                        note = PRRC1(2) siRNA antisense
source                  1..21
                        mol_type = other RNA
                        organism = synthetic construct
SEQUENCE: 6
ttcacctcca gatttgatat t                                              21

SEQ ID NO: 7            moltype = RNA  length = 21
FEATURE                 Location/Qualifiers
misc_RNA                1..21
misc_feature            1..21
                        note = S100A11 siRNA sense
source                  1..21
                        mol_type = other RNA
                        organism = synthetic construct
SEQUENCE: 7
gaactagctg ccttcacaat t                                              21
```

-continued

```
SEQ ID NO: 8           moltype = RNA   length = 21
FEATURE                Location/Qualifiers
misc_feature           1..21
                       note = S100A11 siRNA antisense
source                 1..21
                       mol_type = other RNA
                       organism = synthetic construct
misc_RNA               1..21
SEQUENCE: 8
ttgtgaaggc agctagttct t                                              21
```

COMPOSITION FOR PREVENTING OR TREATING KELOIDS OR HYPERTROPHIC SCARS

RELATED APPLICATIONS

This application is a Division of U.S. patent application Ser. No. 16/639,760 filed on Feb. 18, 2020, which is a National Phase of PCT Patent Application No. PCT/KR2019/017039 having International filing date of Dec. 4, 2019, which claims the benefit of priority of Korean Patent Application No. 10-2019-0117157 filed on Sep. 24, 2019. The contents of the above applications are all incorporated by reference as if fully set forth herein in their entirety.

Sequence Listing Statement

The XML file, entitled 94730SequenceListing.xml, created on Nov. 21, 2022, comprising 12,343 bytes, submitted concurrently with the filing of this application is incorporated herein by reference. The sequence listing submitted herewith is identical to the sequence listing forming part of the international application.

FIELD AND BACKGROUND OF THE INVENTION

The present invention relates to a composition for preventing or treating keloids or hypertrophic scars.

When a dermal layer located deep in the skin is damaged due to surgery or trauma, collagen needed to maintain tension of the skin proliferates excessively in the dermal layer so that the collagen emerges from the thin skin even after a wound has healed, leaving a wound-healed scar in the skin, which is referred to "normal scar." This appears as a result of wound healing, but hypertrophic scars or keloids may appear because fibrous tissues grow abnormally in a compact manner when the skin has a dysfunction in properly regulating and inhibiting a wound healing process. The hypertrophic scars are different from the keloids in that the hypertrophic scars do not extend beyond a wound area and tend to gradually disappear over time, but the keloids grow wider than a damaged area and penetrate into a normal skin over time. There have been various attempts to treat the hypertrophic scars or keloids, including surgical therapy, radiotherapy, steroid therapy, occlusive dressing with silicone gel, laser therapy, and the like, but these methods have limited effects. Accordingly, there are no established methods.

It was known that hypertrophic scars or keloids are formed due to the excessive accumulation of collagen when movement of cells is overactivated during a wound healing process, or when the collagen is formed excessively or is not degraded normally as the cells and capillary vessels proliferate abnormally. Registered Korean Patent No. 10-1505294 discloses a starfish-enriched liquid extract that may be used to hydrolyze collagen to reduce the formation of scars, and Registered Korean Patent No. 10-1697396 discloses a method of treating a hypertrophic scar using a compound that targets a connective tissue growth factor (CTGF) associated with fibrosis.

There is little information on biomarkers that participate in formation of collagen, which excessively accumulates during the wound healing process, and proliferation of cells. By selecting such a biomarker to exactly diagnose an abnormal scar such as a hypertrophic scar and screening a material targeting the biomarker, there is a possible treatment which inhibits the formation of hypertrophic scars or keloids.

SUMMARY OF THE INVENTION

Therefore, it is an object of the present invention to provide a pharmaceutical composition for preventing or treating keloids or hypertrophic scars.

It is another aspect of the present invention to provide a method of preventing or treating keloids or hypertrophic scars.

It is still another aspect of the present invention to provide a method of screening a material for preventing or treating keloids or hypertrophic scars.

It is yet another aspect of the present invention to provide a method of diagnosing keloids or hypertrophic scars.

Technical Solution

To achieve the above objects, the present inventors have assumed that a protein marker having an abnormal expression pattern causes a hypertrophic scar by comparing a difference in expression of various proteins observed in hypertrophic scar tissues and normal tissues, and selected proteins having an expression pattern different from those in the normal tissues.

Accordingly, one aspect of the present invention provides a composition for diagnosing keloids or hypertrophic scars, which includes a material used to measure an expression level of one or more genes selected from the group consisting of TXNDC5, PRRC1, S100A11, Galectin 1, Filamin A, eIF-5A, Annexin A2, and FABP5 or an expression level of one or more proteins selected from the group consisting of TXNDC5, PRRC1, S100A11, Galectin 1, Filamin A, eIF-5A, Annexin A2, and FABP5.

Another aspect of the present invention provides a method of diagnosing keloids or hypertrophic scars, which includes:
  measuring an expression level of one or more genes selected from the group consisting of TXNDC5, PRRC1, S100A11, Galectin 1, Filamin A, eIF-5A, Annexin A2, and FABP5 or an expression level of one or more proteins selected from the group consisting of TXNDC5, PRRC1, S100A11, Galectin 1, Filamin A, eIF-5A, Annexin A2, and FABP5 in keloid or hypertrophic scar tissues; and
  comparing the results of measurement with the expression levels of the genes or proteins in normal tissue.

The measurement of the expression levels of the genes or proteins may be carried out using various methods known in the related art. For example, the measurement may be carried out using RT-PCR (Sambrook et. al., *Molecular Cloning. A Laboratory Manual,* 3rd ed. Cold Spring Harbor Press (2001)), Northern blotting (Peter B. Kaufman et al., *Molecular and Cellular Methods in Biology and Medicine,* 102-108, CRC press), a hybridization reaction using a cDNA microarray (Sambrook et. al., *Molecular Cloning. A Laboratory Manual,* 3rd ed. Cold Spring Harbor Press (2001)), Western blotting, or an in situ hybridization reaction (Sambrook et. al., *Molecular Cloning. A Laboratory Manual,* 3rd ed. Cold Spring Harbor Press (2001)).

Also, the present inventors have confirmed the expression of the selected proteins in keloid or hypertrophic scar tissues and normal tissues using Western blotting and immunohistochemical staining. It was confirmed that when each of genes encoding the proteins is knocked down in the keloid or hypertrophic scar tissues, the expression of collagen type I, α-SMA and PCNA proteins was reduced. These results support that inhibition of the proteins or the knockdown of the genes encoding the proteins is very useful in treating keloids or hypertrophic scars.

Accordingly, still another aspect of the present invention provides a pharmaceutical composition for preventing or treating keloids or hypertrophic scars, which includes, as an active ingredient, a material that inhibits the expression of one or more genes selected from the group consisting of TXNDC5, PRRC1, S100A11, Galectin 1, Filamin A, eIF-5A, Annexin A2, and FABP5 or inhibits the activity of one or more proteins selected from the group consisting of TXNDC5, PRRC1, S100A11, Galectin 1, Filamin A, eIF-5A, Annexin A2, and FABP5.

Yet another aspect of the present invention provides a method of treating a subject having a keloid disease or hypertrophic scar, which includes:
  (a) administering a pharmaceutical composition, which comprises, as an active ingredient, a material that inhibits the expression of one or more genes selected from the group consisting of TXNDC5, PRRC1, S100A11, Galectin 1, Filamin A, eIF-5A, Annexin A2, and FABP5 or inhibits the activity of one or more proteins selected from the group consisting of TXNDC5, PRRC1, S100A11, Galectin 1, Filamin A, eIF-5A, Annexin A2, and FABP5, to the subject having a hypertrophic scar or keloid wound.

In the present invention, the material that inhibits the expression of one or more genes selected from the group consisting of TXNDC5, PRRC1, S100A11, Galectin 1, Filamin A, eIF-5A, Annexin A2, and FABP5 may include short hairpin RNA (shRNA), small interfering RNA (siRNA), microRNA (miRNA), Crispr/Cas9, Crispr/Cpf1, a ribozyme, a DNAzyme, a peptide nucleic acid (PNA), an antisense oligonucleotide, and the material that inhibits the activity of the proteins expressed by the genes may include an antibody, an aptamer, a natural extract, or a chemical. In this case, any material may be included without limitation as long as it is a material that inhibits the expression of the genes and the activity of the proteins.

The term "short hairpin RNA or shRNA" used in this specification refers to single-stranded RNA having a length of 45 to 70 nucleotides. Here, an oligo DNA serving to connect a 3- to 10-base linker between a sense strand of a siRNA base sequence of a target gene and a nonsense strand complementary to the sense strand is synthesized, and then cloned into a plasmid vector, or shRNA is inserted into a retrovirus such as a lentivirus and an adenovirus, and expressed to form shRNA having a looped hairpin structure. Then, the shRNA is converted into siRNA by an intracellular dicer to show an RNAi effect.

The term "siRNA" used in the present invention refers to a nucleic acid molecule that may mediate RNA interference or gene silencing (see WO 00/44895, WO 01/36646, WO 99/32619, WO 01/29058, WO 99/07409, and WO 00/44914). Because the siRNA may inhibit the expression of a target gene, the siRNA is provided for an effective gene knockdown method or a gene therapy method. Although siRNA was first found in plants, insects, Drosophila, and parasites, a variety of siRNAs have been developed and used for application to mammalian cell research (Degot S, et al. 2002; Degot S, et al. 2004; Ballut L, et al. 2005).

A siRNA molecule of the present invention may have a structure in which a sense strand (a sequence corresponding to an mRNA sequence of each gene) and an antisense strand (a sequence complementary to an mRNA sequence of each gene) are located opposite each other to form a double stranded structure. Alternatively, the siRNA molecule of the present invention may have a single chain structure having a self-complementary sense strand and an antisense strand. The siRNA may include, but is not limited to, a complete pair of a double-stranded RNA region forming RNA pairs, as well as unpaired regions formed by a mismatch (the corresponding bases are not complementary to each other), a bulge (there are no corresponding bases in a one-way strand), and the like. The full length of siRNA is in a range of 10 to 100 bases, preferably 15 to 80 bases, more preferably 20 to 70 bases, and most preferably 20 to 30 bases.

The term, "microRNA or miRNA" used in this specification refers to a single-stranded RNA molecule having a length of 21 to 25 nucleotides, and is a regulatory substance that controls the expression of genes in eukaryotes by inhibiting a target mRNA in a disruption or translation phase. Such miRNA is formed by two-step processing. A primary miRNA transcript is cleaved in the nuclei by an RNase III type enzyme referred to as Drosha, resulting in a stem-loop structure consisting of 70 to 90 bases, that is, premiRNA. Then, the premiRNA is translocated into the cytoplasm, and cleaved by an enzyme referred to as a dicer to form mature miRNA consisting of 21 to 25 bases. The miRNA thus formed complementarily binds to a target mRNA to serve as a post-transcriptional gene suppressor and induce translational inhibition and mRNA destabilization. The miRNA is involved in various physiological phenomena and the onset of diseases.

The term "antisense oligonucleotide" used in this specification refers to DNA or RNA, or a derivative thereof, which contains a nucleic acid sequence complementary to a certain mRNA sequence, and serves to bind to a complementary sequence in the mRNA in order to inhibit translation of mRNA into a protein. The antisense sequence of the present invention refers to a DNA or RNA sequence that is complementary to each of the genes, and may bind to mRNA of each of the genes. In this case, the antisense sequence may inhibit essential activities of translation of mRNA of each of genes, translocation into the cytoplasm, maturation, or other overall biological functions. An antisense nucleic acid sequence may have a length of 6 to 100 bases, preferably 8 to 60 bases, and more preferably 10 to 40 bases.

According to one embodiment of the present invention, the material may be siRNA. More specifically, siRNA used to cause the knockdown of TXDNC-5 may consist of sense 5'-GGCCCUAACUAGAGUUCUAtt-3' (SEQ ID NO: 1) and antisense 5'-UAGAACUCUAGUUAGGGCCtt-3' (SEQ ID NO: 2); two siRNAs used to cause the knockdown of PRRC1 may consist of sense 5'-CAAGAAGACCCUA-GAAUUAtt-3' (SEQ ID NO: 3) and antisense 5'-UAAUUC-UAGGGUCUUCUUGtt-3' (SEQ ID NO: 4), and sense 5'-UAUCAAAUCUGGUGAAtt-3' (SEQ ID NO: 5) and antisense siRNA UUCACCUCCAGAUUUGAUAtt-3' (SEQ ID NO: 6); and siRNA used to cause the knockdown of S100A11 may consist of sense GAACUAGCUGC-CACAAtt-3'(SEQ ID NO: 7) and antisense 5'-UU-GUGAAGGCAGCUAGUUCtt-3'(SEQ ID NO: 8).

In this specification, the term "treatment" refers to (i) prevention of keloids or hypertrophic scars; (ii) inhibition of formation or improvement of keloids or hypertrophic scars; and (iii) alleviation of disorders or diseases associated with the inhibition of formation or improvement of keloids or hypertrophic scars. Therefore, in this specification, the term "therapeutically effective amount" refers to an amount sufficient to achieve the pharmacological effect.

According to another aspect of the present invention, the present invention provides a pharmaceutical composition for preventing or treating keloid diseases or hypertrophic scars, which includes (a) a therapeutically effective amount of, as an active ingredient, a material that inhibits the expression of one or more genes selected from the group consisting of TXNDC5, PRRC1, S100A11, Galectin 1, Filamin A, eIF-5A, Annexin A2, and FABP5 or inhibits the activity of one or more proteins selected from the group consisting of TXNDC5, PRRC1, S100A11, Galectin 1, Filamin A, eIF-5A, Annexin A2, and FABP5; and (b) a pharmaceutically acceptable carrier.

The pharmaceutically acceptable carrier included in the composition of the present invention is typically used in preparations, and includes lactose, dextrose, sucrose, sorbitol, mannitol, starch, acacia gum, calcium phosphate, alginates, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but the present invention is not limited thereto. In addition to the aforementioned components, the pharmaceutical composition of the present invention may further include a lubricant, a wetting agent, a sweetening agent, a flavoring agent, an emulsifying agent, a suspending agent, a preservative, and the like.

The pharmaceutical composition of the present invention is preferably parenterally administered. For example, the pharmaceutical composition may be administered by intravenous, intraperitoneal, intratumoral, intramuscular, subcutaneous, hepatoportal, hepatoarterial, or local administration.

An appropriate dose of the pharmaceutical composition of the present invention may vary depending on factors such as a preparation method, a mode of administration, the age, weight, and sex of a patient, the severity of symptoms of a disease, a diet, duration of administration, a route of administration, a secretion rate, and responsiveness. Generally, a skilled physician may easily determine and prescribe the dose of the composition effective for desired treatment.

The pharmaceutical composition of the present invention may be formulated using a pharmaceutically acceptable carrier and/or excipient, according to methods which may be easily carried out by a person having ordinary skill in the art to which the present invention belongs, so that the pharmaceutical composition is prepared in a unit dosage form, or may be prepared by incorporation into a high-dose container. In this case, a formulation may be in the form of a solution, a suspension or an emulsion in an oily or aqueous medium, or in the form of an extract, a powder, a granule, a tablet or a capsule, and may further include a dispersing agent or a stabilizing agent.

The pharmaceutical composition of the present invention may be used as a skin preparation for external use for alleviating or treating keloids or hypertrophic scars. In this case, the formulation is used without particular limitation depending on the body part. Specifically, the pharmaceutical composition may be, for example, a cosmetic composition having a formulation such as a skin softener, a nutrition toner, a massage cream, a nutrition cream, a pack, a gel, or a skin-adhesive type cosmetic product. Also, the pharmaceutical composition may be a formulation for percutaneous administration such as a lotion, an ointment, a gel, a cream, a patch, or a spray. For the composition for external use with each formulation, a person having ordinary skill in the art may properly select and blend the other components other than the aforementioned components in the pharmaceutical composition of the present invention without any difficulty, depending on other factors such as an external formulation for skin, a purpose of use, or the like. In this case, the pharmaceutical composition may have a synergistic effect when the components are used together with the other base materials.

Also, the present invention provides a method of screening a material for preventing or treating keloid diseases or hypertrophic scars, which includes the following steps:
(a) treating keloid tissues or keloid cells with a test material; and
(b) analyzing the activity of one or more intracellular proteins selected from the group consisting of TXNDC5, PRRC1, S100A11, Galectin 1, Filamin A, eIF-5A, Annexin A2, and FABP5 in the tissues or cells treated with the test material or analyzing an expression level of genes encoding the proteins, wherein the test material is judged to be a material for preventing or treating keloids or hypertrophic scars when the activity of the proteins or the expression pattern of the genes encoding the proteins in normal tissues is different from that in the tissues or cells treated with the test material.

According to the method of the present invention, first of all, a test material to be tested is brought into contact with keloid or hypertrophic scar tissues. In describing a screening method of the present invention, the term "test material" used herein refers to an unknown material that is used for screening in order to check whether it has an influence on an expression level of the genes or an amount or activity of the proteins. The test material includes chemicals, nucleotides, antisense RNA, shRNA, miRNA, small interfering RNA (siRNA), and natural extracts, but the present invention is not limited thereto.

Next, the intracellular expression levels of the genes and proteins thereof are analyzed in the tissues or cells treated with the test material. As a result of measurement, when the intracellular expression of genes is reduced, or the activity or expression of the proteins is reduced, the test material may be judged to be a material for preventing or treating keloids or hypertrophic scars.

According to the present invention, by identifying a protein which is involved in abnormal collagen formation in a wound area that may cause keloid or hypertrophic scars, the hypertrophic scars can be accurately diagnosed using the corresponding protein and a gene encoding the protein. Also, a material that inhibits the expression and activity of the proteins or genes can be provided, and thus effectively used to alleviate and treat the keloid or hypertrophic scars.

DESCRIPTION OF SPECIFIC EMBODIMENTS OF THE INVENTION

Hereinafter, the present invention will be described in further detail with reference to embodiments thereof. However, it will be apparent to those skilled in the art that that the description proposed herein is just a preferable example for the purpose of illustration only and is not intended to limit the scope of the present invention.

Examples

Preparation of Human Skin Fibroblasts, Normal Tissues, and Hypertrophic Scar Tissues Skin tissues used in this experiment were obtained from a total of three patients, and an immunohistochemical (IHC) experiment was conducted using male and female normal tissues and scar tissues. Then, an effect of siRNA transformation was observed using primary fibroblast cells derived from each of the tissues.

A tissue was washed with 70% ethanol, and fats were removed by trimming. Then, the tissue was chopped to separate a tissue for the IHC experiment. The remaining tissue was further trimmed, and then chopped. A mixed solution including collagenase, trypsin, and EDTA was added to the tissue, and the cells were isolated by centrifugation at 37° C. and 100 rpm. The isolated cells were cultured in an F12 medium supplanted with 10% fetal bovine serum (FBS) and gentamycin.

Comparison of Expression of Candidate Proteins Via Immunohistochemical (IHC) Experiment on Hypertrophic Scar Tissues A tissue obtained by biopsy was added to an O.C.T compound (Cell Poth, KMA-0100-00A), and frozen in dry ice. The frozen tissue was fixed in a buffer containing acetone and methanol at a ratio of 1:1. After the buffer was removed, the tissue was permeabilized by treatment with 0.5% Triton X-100 at room temperature for 10 minutes, and peroxidase activity was then inhibited using Ultravision hydrogen peroxide (Thermo kit/Ultravision LP detection system). The tissue was reacted with an Ultravision block buffer at room temperature for 10 minutes, and then treated with the corresponding primary antibody, and treated overnight at 4° C. Each of TXNDC5 (Abcam, Ab155684), PRRC1 (Abcam/ab12544), S100A11 (Abcam/ab97329), Galectin 1 (Abcam, Ab108389), Filamin A (Millipore/MAB1680), eIF5-A (Abcam/ab32014), Annexin A2 (Cell Signaling/8235), and FABP5 (Abcam/ab37267) was used as the primary antibody. The tissue was treated with a primary antibody enhancer at room temperature for 10 minutes, and a HRP polymer was reacted at room temperature for 15 minutes in the dark. After the HRP polymer was removed, all the tissues except for PRRC1 were treated with AEC (Spring, ASS-125), and PRRC1 was treated with DAB (Thermo, TA-125-HDX) for a minute. The tissues were stained with Mayer's hematoxylin at room temperature, dehydrated, and then mounted with Canada balsam-mixed xylene. Then, the tissues were observed using a microscope.

Figure 1:
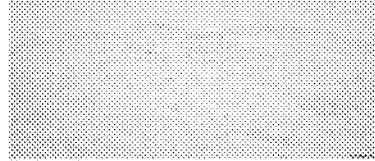
FIG. 1 shows the results of immunohistochemical staining for candidate proteins of human hypertrophic scar tissue.

The IHC results showed that TXNDC5, PRRC1, S100A11, Galectin 1, Filamin A, eIF-5A, Annexin A2, and FABP5 had a pattern of increased expression in the hypertrophic scar tissues, compared to the normal tissues. The pattern of increased expression varied depending on the locations of the dermis, the epidermis, and other layers. The results of difference in expression of the candidate proteins are listed in Table 1 and shown in FIG. 1 below.

TABLE 1

Results of comparison of expression and location of human fibroblast normal/scar pair proteins

| Candidate | Results of difference in expression |
| --- | --- |
| TXNDC5 | Increased expression in scar epidermis and dermis |
| PRRC1 | Increased expression in scar epidermis and dermis |

TABLE 1-continued

Results of comparison of expression and location of human fibroblast normal/scar pair proteins

| Candidate | Results of difference in expression |
| --- | --- |
| S100A11 | Increased expression in scar epidermis and dermis |
| Galectin 1 | Increased expression in scar dermis |
| Filamin A | Increased expression in scar epidermis and dermis |
| eIF-5A | Increased expression in scar epidermis and dermis |
| Annexin A2 | Increased expression in scar epidermis and dermis |
| FABP5 | Increased expression in scar epidermis |

Change in Effect of Candidate Protein-Specific siRNA Transformation—Changes in Expression of Collagen Type I and α-SMA and PCNA in Fibroblasts of Hypertrophic Scar Tissues For three (TXNDC5, PRRC1, and S100A11) of the proteins selected from the IHC results, expression of proteins associated with proliferation of collagen and fibroblasts, which were excessively expressed in a scar when the expression of each of the genes was knocked down using siRNA, was analyzed.

Specifically, sense 5'-GGCCCUAACUAGAGUUCUAtt-3' (SEQ ID NO: 1) and antisense 5'-UAGAACUC-UAGUUAGGGCCtt-3' (SEQ ID NO: 2) were used as siRNA used to cause the knockdown of TXDNC-5; sense 5'-CAAGAAGACCCUAGAAUUAtt-3' (SEQ ID NO: 3) and antisense 5'-UAAUUCUAGGGUCUUCUUGtt-3' (SEQ ID NO: 4), and sense 5'-UAUCAAAUCUG-GUGAAtt-3' (SEQ ID NO: 5) and antisense siRNA UUCACCUCCAGAUUUGAUAtt-3' (SEQ ID NO: 6) were used as two siRNAs used to cause the knockdown of PRRC1; and sense GAACUAGCUGCCACAAtt-3' (SEQ ID NO: 7) and antisense 5'-UUGUGAAGGCAGC-UAGUUCtt-3' (SEQ ID NO: 8) were used as siRNA used to cause the knockdown of S100A11.

Specifically, fibroblasts isolated from hypertrophic scar tissues were cultured in an F12 medium supplemented with 10% FBS, and then transfected with the siRNA knocking down the corresponding protein. After 48 hours of siRNA transfection, a cell lysate was extracted, and then subjected to Western blotting to check a change in expression of collagen, and the like.

Figure 2:
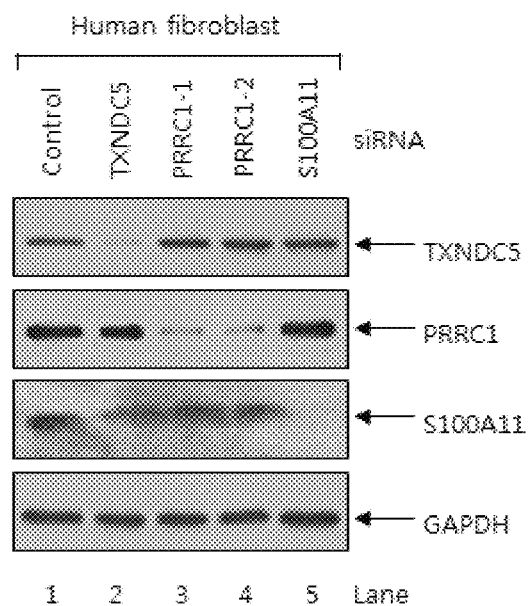
FIG. 2 shows the results of determining protein knockdown efficiency when siRNA targeting three candidate proteins is treated, using Western blotting.

As a result, it was confirmed that the target protein was knocked down by the siRNA transfection (FIG. 2), and an effect of the knockdown of the target protein on the functions and growth of fibroblasts was checked with a change in expression of the collagen-1, α-SMA, and PCNA proteins.

Figure 3:
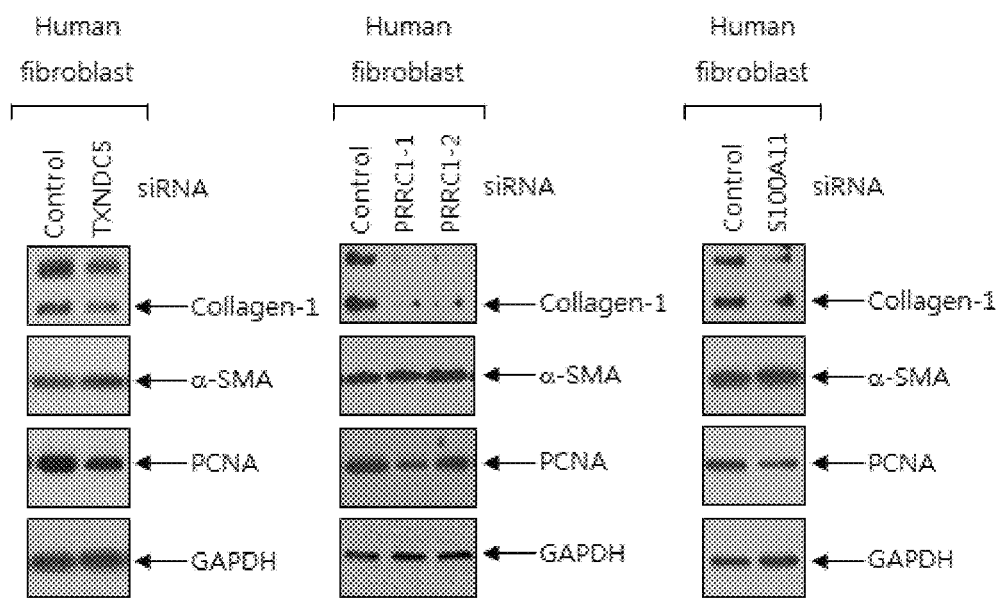
FIG. 3 shows the results of determining an expression pattern of collagen in hypertrophic scar tissues in which the candidate protein is knocked down, using Western blotting.

Based on the results of observation, it was confirmed that the expression of the collagen-1, α-SMA, and PCNA proteins was inhibited when the expression of all the three genes was inhibited (FIG. 3).

As a result, it was confirmed that, by inhibiting each of the candidate proteins, since the synthesis of collagen excessively formed in the hypertrophic scars was inhibited, the growth of fibroblasts was effectively inhibited and apoptosis was induced, the candidate proteins were found to be targets for alleviating or treating the hypertrophic scars.

While the present invention has been shown and described with reference to certain exemplary embodiments thereof, it will be understood by those skilled in the art that various changes in form and details may be made therein without departing from the scope of the invention as defined by the appended claims. Therefore, it will be understood that the practical scope of the present invention is defined by the appended claims and equivalents thereof.

What is claimed is:

1. A method of treating a subject having hypertrophic scar, comprising:
(a) administering a pharmaceutical composition, which comprises, as an active ingredient, siRNA that inhibits the expression of gene encoding PRRC1, wherein the siRNA is selected from the group consisting of SEQ ID NO: 3/SEQ ID NO: 4 and SEQ ID NO: 5/SEQ ID NO: 6, to the subject having hypertrophic scar.

* * * * *